(12) United States Patent
Nebe et al.

(10) Patent No.: US 8,568,987 B2
(45) Date of Patent: Oct. 29, 2013

(54) CHEMOTAXIS DIAGNOSTIC

(75) Inventors: Carl Thomas Nebe, Ladenburg (DE); Karin Hartmann, Ellerstadt (DE)

(73) Assignee: Glycotope Biotechnology GmbH, Heideberg (DE)

( * ) Notice: Subject to any disclaimer, the term of this patent is extended or adjusted under 35 U.S.C. 154(b) by 0 days.

(21) Appl. No.: 12/655,313

(22) Filed: Dec. 29, 2009

(65) Prior Publication Data

US 2010/0159484 A1 Jun. 24, 2010

Related U.S. Application Data

(63) Continuation of application No. 10/204,318, filed as application No. PCT/EP01/02176 on Feb. 26, 2001, now abandoned.

(30) Foreign Application Priority Data

Feb. 28, 2000 (DE) .................................. 100 09 420
Dec. 7, 2000 (DE) .................................. 100 60 880

(51) Int. Cl.
*G01N 33/53* (2006.01)
(52) U.S. Cl.
USPC ............................................ 435/7.1; 435/7.2
(58) Field of Classification Search
None
See application file for complete search history.

(56) References Cited

U.S. PATENT DOCUMENTS

2002/0111476 A1* 8/2002 Franz-Bacon et al. ....... 536/23.5

OTHER PUBLICATIONS

Hennigan et al. Neutrophil heat shock protein expression and activation correlate with increased apoptosis following transmigration through the endothelial barrier. Shock 12(1):32-38, 1999.*
Wheeler et al Comparison of colony stimulation factors on in vitro rat and human neutrophil function. Biol Neonate. 1994;66(4):214-20.*
Martz E. Introduction Flow Cytometry. p. 1-8, Jan. 2000.*
Anderson et al. Diminished lectin-, epidermal growth factor-, complement binding domain-cell adhesion molecule-1 on neonatal neutrophils underlies their impaired CD18-independent adhesion to endothelial cells in vitro. J Immunol. May 15, 1991;146(10):3372-9.*
Imai et al Identification and molecular characterization of fractalkine receptor CX3CR1, which mediates both leukocyte migration and adhesion. Cell. Nov. 14, 1997;91(4):521-30.*
Sabroe et al. Differential Regulation of Eosinophil Chemokine Signaling Via CCR3 and Non-CCR3 Pathways. J Immunol 1999;162;2946-2955.*
Office Action from parallel European Patent Application No. 10 003 707.6 dated Mar. 12, 2013 (6 pages).
English Translation of the Office Action of European Patent Application No. 10 003 707.6-1405 dated Mar. 12, 2013 (5 pages).
Raffaele Badolato et al., "Monocytes from Wiskott-Aldrich patients display reduced chemotaxis and lack of cell polarization in response to monocyte chemoattractant protein-1 and formyl-methionyl-leucyl-phenylalanine," Journal of Immunology (Baltimore, MD.: 1950), 161(2):1026-1033 (Jul. 15, 1998).
Maria E. Klut, et al., "Activation-associated changes in blood and bone marrow neutrophils," Journal of Leukocyte Biology, 62:2:186-194 (Aug. 1997).
Miguel Vicente-Manzanares, et al., "Involvement of Phosphatidylinositol 3-Kinase in Stromal Cell_Derived Factor 1 alpha-induced lymphocyte polarization and chemotaxis," Journal of Immunology (Baltimore, MD.: 1950), 163:7:4001-4012 (Oct. 1, 1999).

* cited by examiner

*Primary Examiner* — Jacob Cheu
(74) *Attorney, Agent, or Firm* — Abelman, Frayne & Schwab

(57) ABSTRACT

A method is described for determining the chemotactic activity of leukocytes in a sample, in which method the expression of a cell adhesion molecule is determined.

12 Claims, 11 Drawing Sheets

Figure 1
The phagocytosis process
 Opsonisation
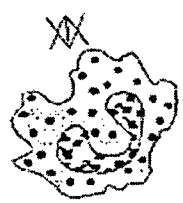 Chemotaxis
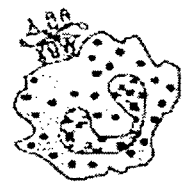 Adsorption
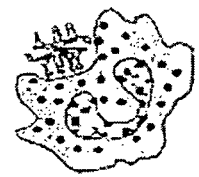 Phagocytosis
 Destruction
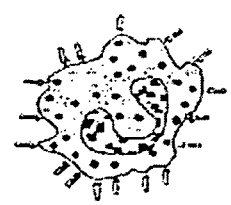 Antigen presentation

Chemotaxis test

1. ENRICHMENT

3. LABELING

Figure 3a: Negative control containing PBS
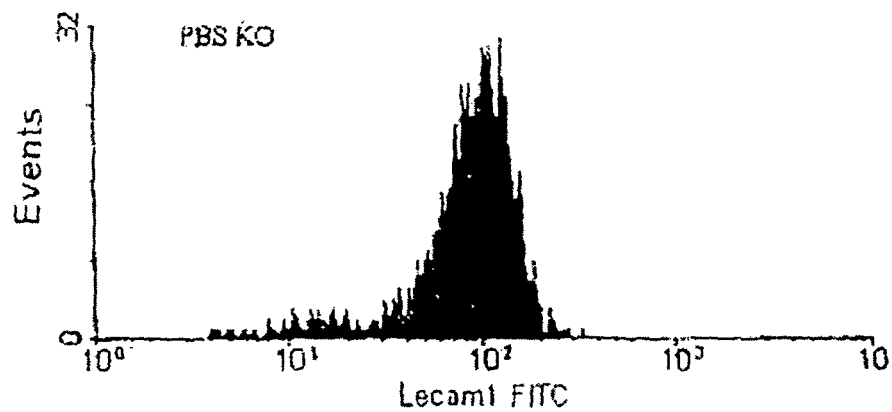
Mean intensity (mean) of Lecam 1 FITC: 93
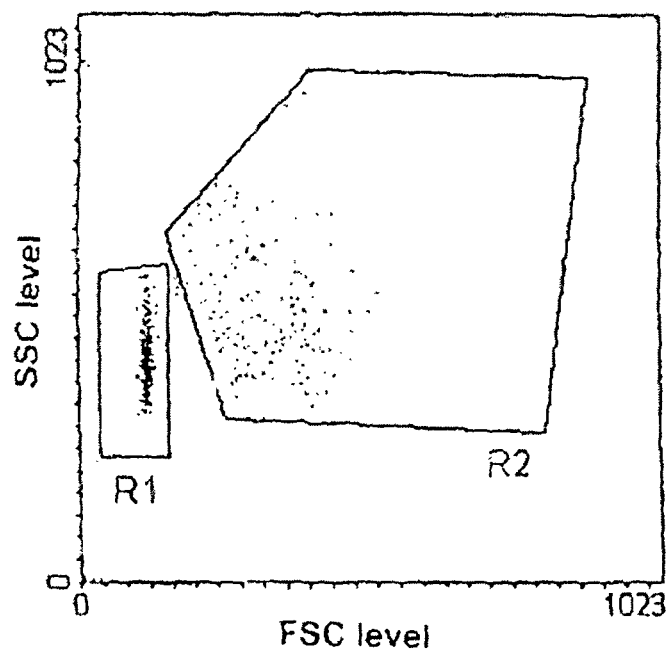
Mean intensity of forward scatter (FSC) : 478

Figure 3b: Assay containing 5 x 10-8 M fMLP
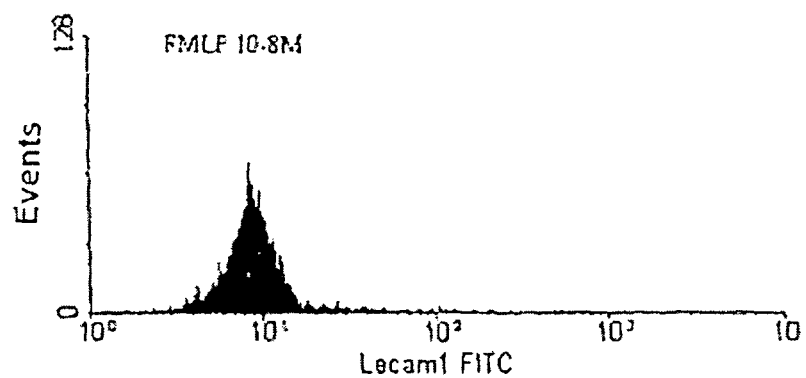
Mean intensity of Lecam 1 FITC: 10
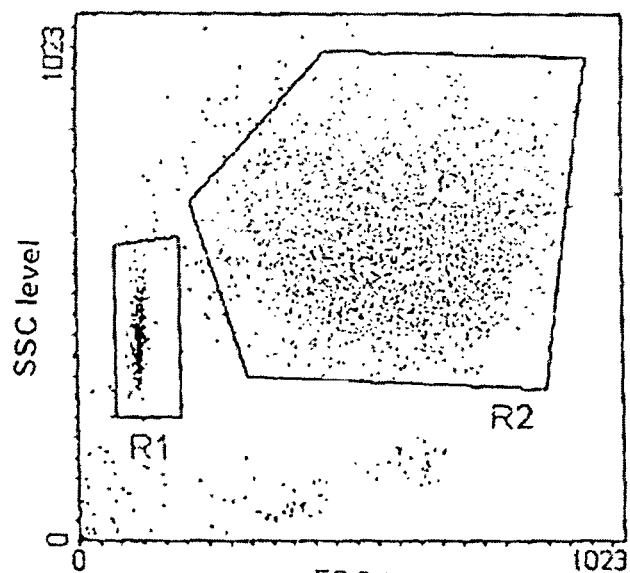
Mean intensity forward scatter (FSC): 634

CHEMOTAXIS DIAGNOSTIC

RELATED APPLICATIONS

This application is a continuation of application Ser. No. 10/204,318, filed Nov. 1, 2002, now abandoned which is a §371 of PCT/EP01/02176 filed Feb. 26, 2001, which claims priority from German Patent Application No. 100 09 420.1 filed Feb. 28, 2000 and German Patent Application No. 100 60 880.9 filed Dec. 7, 2000, all of which are incorporated by reference in their entity.

The invention relates to a method for determining the chemotactic activity of leukocytes, in particular granulocytes, in a sample and to a reagent kit which is suitable for this purpose. The invention also relates to a method for diagnosing an immunological defect and/or a disturbance in granulocyte function.

In order to defend itself from invading foreign bodies, such as microorganisms, and in order to eliminate old and damaged cells or cell debris, a mammalian organism has at its disposal mechanisms which lead to the destruction of these unwanted elements. The bacteria or cells are first of all opsonised, thereby stimulating their phagocytosis by leukocytes. The leukocytes which are capable of phagocytosis at first migrate towards the invading foreign body, a process which is termed chemotaxis. The chemotaxis can be induced by a concentration gradient of particular stimulatory substances, such as for example microbial constituents, complement degradation products or cytokines, which are recognized by specific receptors, so called chemoreceptors. While substances which are chemotactically active in the main bring about a movement in the direction of the higher concentration of stimulatory substance (positive chemotaxis), they also, in rare cases, bring about a movement in the opposite direction (negative chemotaxis). There then follows an adsorption, i.e. the unwanted elements are bound on the surface of the leukocytes which are capable of phagocytosis, i.e. essentially monocytes, macrophages and polymorphonuclear leukocytes. During the subsequent phagocytosis, the element which is recognized as being foreign is enclosed by the cell and subsequently destroyed by degradation.

In order to assess the overall efficiency of the immune system, it is necessary to analyze the number and function of the leukocytes. Counting with the aid of an automated differential hematology counter, while additionally using monoclonal antibodies, is nowadays already a matter of clinical routine. However, because of the large number of different functions which leukocytes possess within the context of immune defense, there is still a need to supplement the existing test options with functional analyses.

As explained above, the phagocytic cells constitute the first line of immune defense and testing them has thus far to a large extent been neglected by comparison with the investigations which have been carried out on lymphocytes. The methods which are described in the literature for analyzing phagocytic performance, for example counting under the microscope, are impractical for daily use in the clinical laboratory since they are labor-intensive and are subjective as far as assessment is concerned. In what is termed the Boyden chamber test, the leukocytes have to migrate through a membrane following a concentration gradient of a chemotaxin. The distance of the migration front, or the cells, on the underside of the membrane is then evaluated microscopically. In addition, the prior art also describes the measurement of the change in the shape of neutrophilic granulocytes, which change also becomes visible cytometrically. However, due to the difficulties associated with implementing these tests, investigations for chemotaxis have thus far been the reserve of specialist laboratories.

In addition to this, it is currently only possible to diagnose, in the laboratory, far less than 50% of the immunological defect which are observed clinically.

An object of the present invention was therefore to provide a method which can be used for investigating other leukocyte functions, in particular chemotaxis.

According to the invention, this object is achieved by means of a method for determining the chemotactic activity of leukocytes in a sample, which method is characterized in that the expression, and, in particular, the change in the expression density, of a cell adhesion molecule is determined.

The test for chemotaxis joins a series of other tests which are required for elucidating the leukocyte function when there is a question of an immunological defect or of an immunostimulation. It has been established that the process of phagocytosis can be broken down into different constituent steps, such as opsonisation, chemotaxis, adsorption, phagocytosis, destruction and antigen presentation. These constituent steps can then be examined individually, resulting in it being possible to analyze and determine the different functions of the leukocytes.

Chemotaxis is relatively frequently affected in connection with disturbances in granulocyte function and is said to be impaired in connection with about 50% of congenital immunological defects.

It has now been found, surprisingly, that a change in the expression density of particular leukocyte cell adhesion molecules takes place in parallel with the chemotactic function of leukocytes and of granulocytes in particular. By determining or analyzing the expression of a cell adhesion molecule it is consequently possible to provide a reproducible test which is suitable for daily clinical laboratory routine and which makes it possible to quantify the chemotactic function of leukocytes, in particular granulocytes, in a comparatively simple manner. With the aid of flow-through cytometry, the method according to the invention is objectively quantifiable and reproducible.

The method according to the invention can be used to determine the chemotactic activity of leukocytes, in particular of granuloctyes, lymphocytes and/or monocytes.

The method according to the invention is suitable, in particular, for determining the chemotactic activity of neutrophilic granulocytes. The task of the neutrophilic granuloctyes is to eliminate invading bacteria and dead endogenous cells by phagocytosis, usually within the context of an inflammatory reaction.

Cell adhesion molecules are receptor molecules which are found on the surfaces of cells. For the most part, cell adhesion molecules are glycoproteins which bind specifically to other cells or interact with constituents of the extracellular matrix (ECM). The cell adhesion molecules which are present on cells of the immune system are in particular those which are responsible for adhesion to target cells. Endothelial leukocyte adhesion molecule 1 (ELAM-1) is structurally related to certain lectins, to the epidermal growth factor and to complement regulating proteins from the selectin or LECAM superfamily and is involved, for example, in the adhesion of leukocytes to inflammatory foci.

Preference is given to determining the expression of a cell adhesion molecule which comprises a lectin domain, in particular of a cell adhesion molecule selected from L-selectin, CD62, in particular CD62L or CD62b, LECAM-1, Mel-14, LAM-1, Leu-8, TQ1, LEC.CAM-1, DREG56, GMP-140 and ELAM. In a particularly preferred embodiment, expression of the cell adhesion molecule LECAM-1 is determined. The change in the density at which the cell adhesion molecule LECAM is expressed correlates directly with the activation of neutrophilic granulocytes following the binding of chemotaxin. The change in expression takes place in an almost binary manner, from a state of high expression density to a state of low density following activation. Intermediate states therefore produce two peaks in the histogram or CD62 expression. Therefore, in a preferred embodiment, the decrease in the expression density of a cell adhesion molecule, selected from L-selectin, CD62, in particular CD62L or CD62b, LECAM-1, Mel-14, LAM-1, Leu-8, TQ1, LEC.CAM-1, DREG56, GMP-140 and ELAM, preferably and in particular of LECAM, on the surface of the leukocyte cells, in particular granulocytes, which decrease accompanies the increase in the chemotactic activity, is determined.

In another preferred embodiment, the expression, and, in particular, the change, preferably an increase, in the expression density, of the adhesion molecule CD11b, is determined. It has been found that the density at which the adhesion molecule CD11b is expressed is up-regulated after a chemotaxin has been bound. However, this effect is not as pronounced as the down-regulation of CD62L, which means that greater preference is given to determining CD62L.

For determining expression, preference is given to using a binding molecule which is specific for the cell adhesion molecule, in particular a specific antibody. The expression can then be rendered visible by means of suitable labeling groups, such as fluorescent labels, latex beads, enzyme labels or the like. It is possible to use either direct or indirect labels.

In a preferred embodiment, the sample is preincubated with a chemotaxis stimulant. The chemotaxis stimulant which is preferably used is a chemotactic peptide for stimulating leukocytes, in particular granulocytes. Examples of suitable chemotactic peptides are peptides which possess an N-terminal N-formyl radical, in particular peptides selected from the group comprising fMLP (N-formyl-Met-Leu-Phe) or structural analogs thereof, e.g. N-formyl-Met-Leu-Phe-benzylamide, N-formyl-Met-Leu-Phe-methyl ester, N-formyl-Met-Leu-Phe-Phe, N-formyl-Met-Phe and N-formyl-NorLeu-Leu-Phe. Particular preference is given to using fMLP and/or interleukin-8 (IL-8) as the chemotaxis stimulant. The final concentration of the chemotaxis stimulant, in particular of a chemotactic peptide, in the sample is preferably from $10^{-9}$ to $10^{-5}$ mol/l, preferably from $10^{-8}$ to $10^{-6}$ mol/l, in particular about $5 \times 10^{-8}$ mol/l. The incubation with the chemotaxis stimulant preferably takes place at a temperature of from 20 to 50° C., in particular of from 30 to 40° C., particularly preferably of from about 36 to 38° C., for from 2 to 120 minutes, preferably for from 5 to 60 minutes, in particular for from 10 to 30 minutes and particularly preferably for about 20 minutes. It is also possible to carry out the method according to the invention in several parallel assays using different incubation times and/or at different incubation temperatures, such that a time kinetics can be measured, thereby enabling further conclusions to be drawn with regard to the chemotactic activity.

The determination of the expression of the cell adhesion molecule can be evaluated using suitable methods, for example a flow-through cytometer, an image analysis system (e.g. microscope-based) or in a spectrofluorimeter (also suitable for microtiter plates). The determination preferably takes place in a flow-through cytometer, thereby enabling an evaluation which is objectively quantifiable and reproducible to be achieved.

Another advantage of the method according to the invention is that the chemotactic activity can be measured either in a prepared body fluid or in a body fluid which is not purified, in particular in whole blood. This can thereby further increase the accuracy of the measurement since purification or preparation steps are not absolutely necessary. Whole blood, and, in particular, anticoagulated, e.g. heparinized, whole blood, is preferably used as the sample for determining the chemotactic activity. The down-regulation of CD62L, in particular, can be readily measured in whole blood.

However, it is also possible to use a prepared body fluid, preferably a leukocyte-rich plasma. When plasma is used, it is also possible to readily measure migration through a membrane in addition to the down-regulation.

The sample which is used is, in particular, a mammalian body fluid, preferably a human sample.

The method according to the invention for determining chemotactic activity can advantageously be combined with other methods for determining leukocyte functions. Further analytical and/or diagnostic information can be obtained in this way.

For example, it is also possible to determine the shape and/or size of the leukocytes, in particular the granulocytes, in a conventional manner. Change in the shape and/or size of the leukocytes is preferably determined in a flow-through cytometer.

In a preferred embodiment of the method according to the invention, the leukocytes, in particular granulocytes, are conducted through a porous membrane after having been incubated with a chemotaxis stimulant. Preference is given to using a porous membrane having a defined orifice diameter.

In this way, it is also possible to determine the number of leukocytes, in particular granulocytes, which have migrated through a porous membrane. The cells are preferably counted by adding latex beads in a flow-through cytometer.

A membrane which permits granulocytes, in particular, to pass through in a very short period of time, something which is very advantageous for the duration of the test and consequently for clinical use, has surprisingly been found. Coating membranes with collagen increases the difference between a control assay without chemotaxis stimulant, e.g. fMLP, and a test assay with chemotaxis stimulant, e.g. fMLP. It was also possible to achieve good results by using membranes which were coated with fibronectin, gelatin or other collagen-related substances.

Methods for measuring chemotaxis which are described in the prior art and which are applied in practice comprise, for example, the use of membranes made of cellulose. In these methods, the distance of the migration front from the starting surface is measured after the cells have been stained panoptically in an appropriate manner. Agarose-coated glass slides represent another alternative. In this case, the cells are aliquoted into one punched hole and fMLP is aliquoted into the other. The neutrophils migrate in the gap between the agar and the glass in the direction of increasing chemotaxin concentration, with the distance of the migration front being measured microscopically after staining. Glass capillaries and agar dishes which are filled with cells represent another alternative for determining chemotaxis, with this alternative being analogous to the slide method. The analyses of chemotaxis using these methods have thus far been the reserve of specialist laboratories. By contrast, the method according to the invention, in particular the simple and reproducible combination of insert and flow-through cytometry, enables chemotaxis to be determined in a simple manner.

The invention therefore also relates to a method for determining the chemotactic activity of leukocytes in a sample, which method is characterized in that the number of leukocytes which have migrated through a porous membrane is determined. The combination of the use of membranes and of cytometry for determining chemotactic activity has not previously been described in the prior art.

This method can be used to determine the chemotactic activity of leukocytes, in particular of granulocytes, lymphocytes and/or monocytes, particularly preferably of neutrophilic granulocytes. Thin membrane disks are preferably used for measuring the migration. Suitable membranes preferably have a pore diameter in the order of magnitude of from 1.0 to 10 μm, more preferably of from 2.0 to 4 μm. Examples of suitable membrane materials are polycarbonate and polyethylene terephthalate.

In one embodiment of this method, it is possible to use what is termed a Boyden chamber. In this case, use is made of a membrane disk, for example a membrane disk made of polycarbonate (e.g. Track-Elch membrane, from Nukleopore, order No. 150444), which is mounted in a blind well chamber, which comprises a centrally bored plastic screw and an acrylic block which is bored and provided with an internal thread. However, in this embodiment, care must be taken to ensure that the lower chamber is filled free of air bubbles, and account must be taken of the pressure ratios between the compartments. Preference is therefore given to using cell culture inserts as porous membranes through which migration is to take place. In particular, manipulation in regard to multiple assays and the filling of the chamber is easy to perform when using cell culture inserts. Examples of suitable cell culture inserts are Nunc tissue culture inserts having a diameter of 10 mm and a pore size of 3.0 μm, with the membranes consisting of polycarbonate, and Falcon cell culture inserts having a diameter of 6.4 mm and a pore size of 3.0 μm. Such cell culture inserts can be used in cell culture plates having wells, for example in 24-well cell culture plates.

However, when porous membranes are used, the difference in the migration through the membranes with and without chemotaxin is frequently small when there is wide variation in the values. A marked improvement in the method can be achieved by providing the porous membrane, in particular cell culture inserts, with a coating. Suitable coatings comprise Tween, polyanions, gelatin, fibronectin and milk powder. The best results were obtained with collagen-coated membranes, for which reason this embodiment is that which is most preferred. The species from which the collagen is derived can be selected at will. For example, human collagen, mouse collagen or calf collagen is suitable.

The collagen-coated porous membranes which are particularly preferably to be used for determining the chemotactic activity of leukocytes in a sample can be prepared, for example, by incubating a suitable membrane, for example a membrane having a pore size of from 1 μm to 10 μm (e.g. composed of polycarbonate or polyethylene terephthalate) with dissolved collagen (for example 1 mg of collagen/ml of 0.1% acetic acid) for from 5 minutes to 2 hours, in particular for from 20 to 40 minutes, and then drying the membrane after having washed it. Collagen-coated cell culture inserts are particularly advantageous as regards the duration of the test assay, and as regards manipulation and the evaluation method. In order to obtain collagen-coated porous membranes, the abovementioned porous membranes can, for example, be coated with human collagen or calf collagen. Polyethylene terephthalate-based cell culture inserts coated with mouse collagen IV can be obtained from Falcon.

Advantageously, use is made of cell culture inserts which taper towards the bottom, thereby preventing wetting on the outside as a result of contact between the plate and the insert.

Particularly advantageously, migration through a porous membrane, in particular through a collagen-coated porous membrane, and determination of the change in the expression density of a cell adhesion molecule, and also, where appropriate, the change in shape (e.g. measured in forward-scattered light), are combined for determining the chemotactic activity of leukocytes. A combination of cytometry and change in expression density provides the advantage that adhesion to endothelial cells can be tested functionally.

Preferably, the change in shape, the decrease in the density at which a cell adhesion molecule, in particular LECAM, is expressed, and the number of leukocytes, in particular granulocytes, which have migrated through the membrane are measured in parallel with increasing sensitivity.

The combination of the three parameters down-regulation of a cell adhesion molecule, e.g. of CD62L, change in the shape of leukocytes, in particular granulocytes, and migration through a membrane represents another part of the subject matter of the invention. This combination yields additional information on chemotactic activity. In this connection, it is to be noted that, while further down-regulation takes place in connection with calcium withdrawal (addition of EDTA), for example, this occurs without any change in the shape of the leukocytes or any migration through a membrane, which means that the three parameters are not necessarily correlated but, instead, provide separate pieces of information which complement each other.

Independently of the implementation of the method according to the invention, it is advantageous to always include a sample from a healthy volunteer for control purposes.

The present invention furthermore relates to a reagent kit for determining the chemotactic activity of leukocytes, in particular granulocytes, which kit is characterized in that it contains a specific binding partner for detecting the expression of a cell adhesion molecule and also a chemotaxis stimulant. Preferably, the two components are physically separated from each other. The components of the reagent kit can, for example, be ready-to-use solutions or else lyophilizates from which the user then prepares the solutions. In addition, the reagent kit can comprise customary buffers and auxiliary substances.

The specific binding partner which is contained in the reagent kit is preferably an antibody directed against the cell adhesion molecule, in particular an antibody directed against the CD62b cluster or CD11b. In addition, the reagent kit can contain a direct or indirect label, in particular a fluorescence label.

The invention furthermore relates to a method for diagnosing an immunological defect and/or a disturbance in leukocyte function, in particular a disturbance in granulocyte function, which method is characterized in that the chemotactic activity of leukocytes in a sample obtained from the patient is determined using the method according to the invention for determining the chemotactic activity, and the chemotactic activity of a negative control sample is determined in another assay, and the presence or absence of an immunological defect and/or of a disturbance in leukocyte function is elucidated by comparing the values which are obtained. Disturbances in leukocyte function are manifested, for example, in recurrent skin abscesses or disturbances in wound healing.

The method according to the invention for determining chemotactic activity, and the reagent kit according to the invention, can likewise be used for diagnosing an immunological defect and/or a disturbance in leukocyte function.

The clinical results which have thus far been obtained with patients show that the density at which the adhesion molecules are expressed is altered, in particular, i.e. the state which is reached in vitro following stimulation is already present in vivo. This results in an impairment of the rolling and the adhesion to the endothelial cells (inner lining of the blood vessels) for the subsequent migration out of the blood vessel (post capillary venules). The actual migration through the membrane is usually not impaired. Enormous importance must therefore be attached to determining the density at which CD62L and CD11b, and also other adhesion molecules, are expressed.

FIG. 1 shows the different steps in the phagocytosis process:
opsonization: using antibodies and
    complement (C3b)
chemotaxis: induced by C5a, for example,
adsorption: binding to receptors FcR I, II, III and C3bR,
phagocytosis: formation of the phagosome,
destruction: fusion with lysosomes,
    killing—not oxygen-dependent
        oxygen-dependent (burst)
antigen
    presentation: processing of the antigen and presentation for T cells via MHC II (e.g. HLA-DR).

FIG. 3 shows the results obtained using a flow-through cytometer.

FIG. 3A shows the negative control containing PBS while FIG. 3B shows an assay containing $5 \times 10^{-8}$ MfMLP. A decrease in the surface expression of the cell adhesion molecule LECAM-1 by about one order of magnitude can be seen. The number of neutrophilic granulocyte cells (region R2) is shown in relation to the constant number of beads (R1), with it being possible, in this case, to see a marked increase, on stimulation (FIG. 3B), in the number of cells which have migrated through the membrane.

FIG. 4 shows diagrams relating to migration through various coated membranes.

Figure 2:
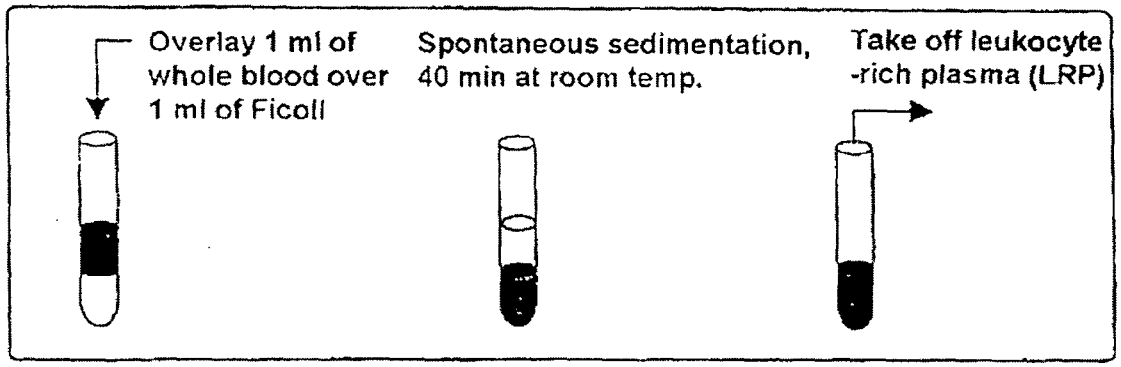
FIG. 2 shows a diagram of the chemotaxis test according to the invention.
Figure 2:
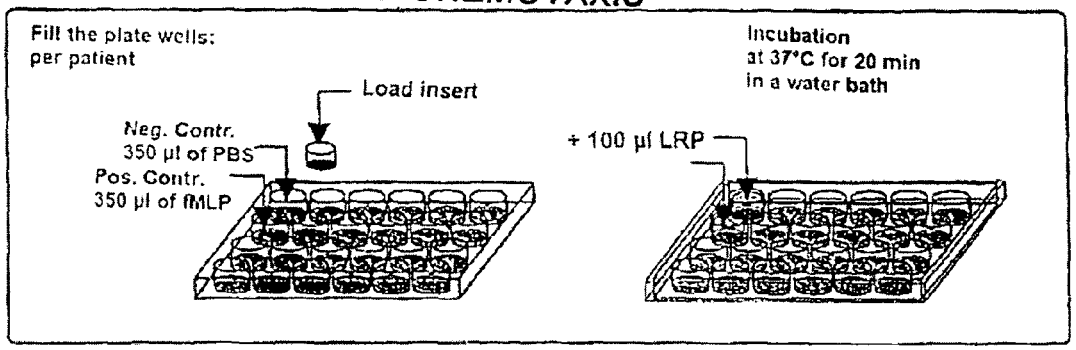
Figure 2:
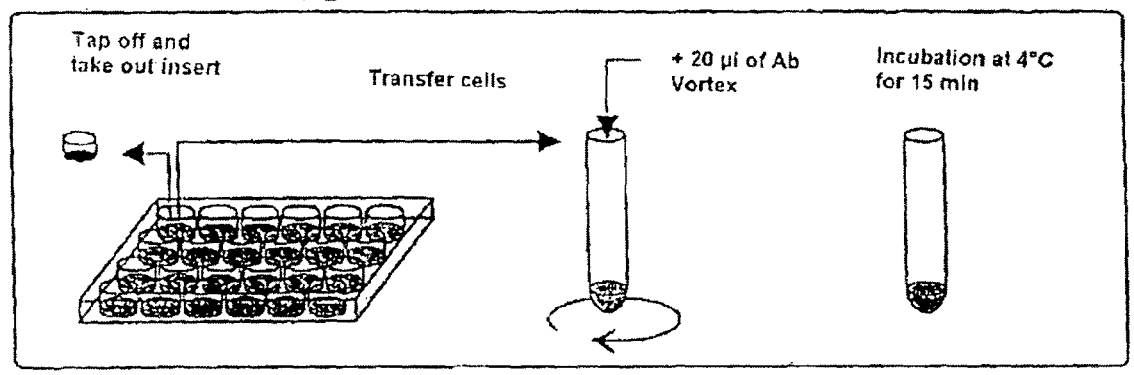
Figure 2:
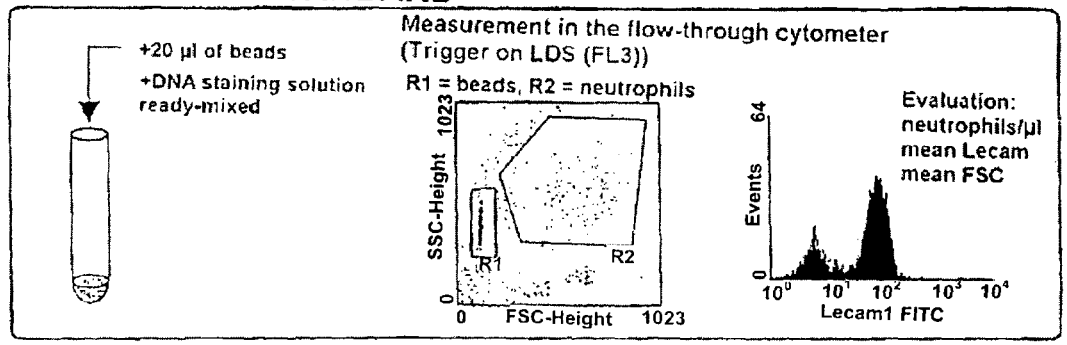
Figure 4A:
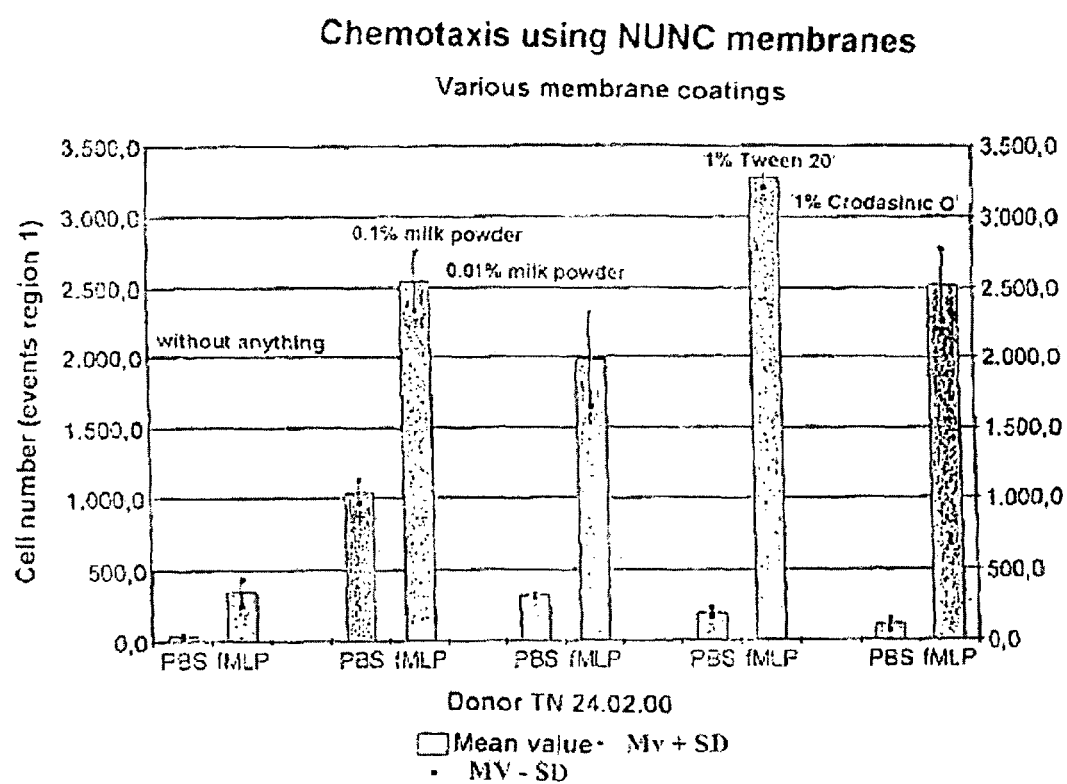

FIG. 4A shows chemotaxis using Nunc polycarbonate membranes which were uncoated or were coated with 0.1% milk powder, with 0.01% milk powder, with 1% Tween 20 or with 1% Crodasinik O. The migration through the membrane was in each case measured in the absence (PBS) and in the presence (fMLP) of a chemotaxis stimulant.

Figure 4B:
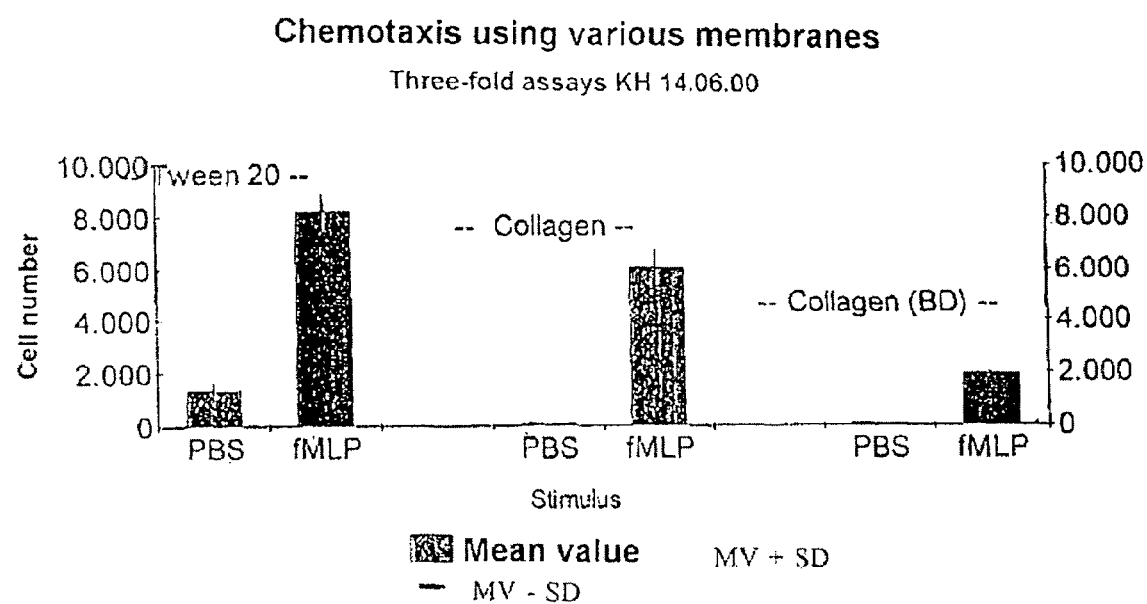

FIG. 4B shows migration through polyethylene terephthalate membranes coated with Tween 20 or collagen.

Figure 5:
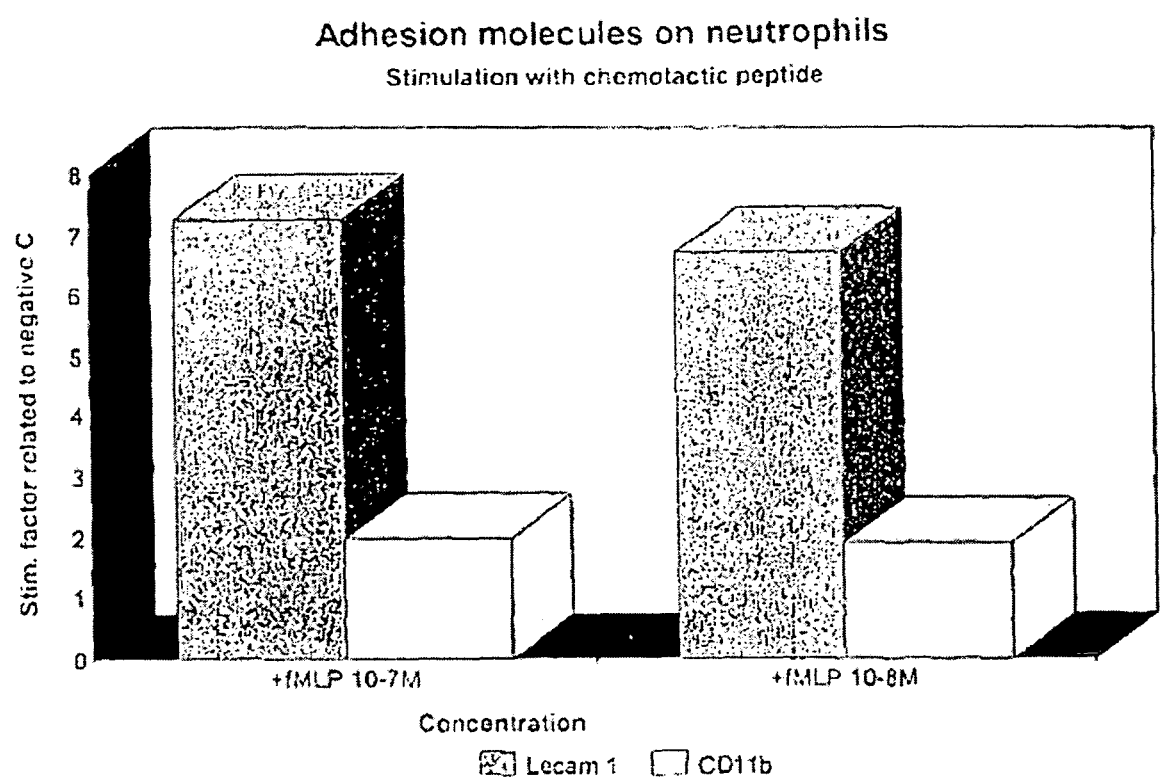

FIG. 5 shows adhesion molecules on neutrophils when stimulated with chemotactic peptide.

Figure 6:
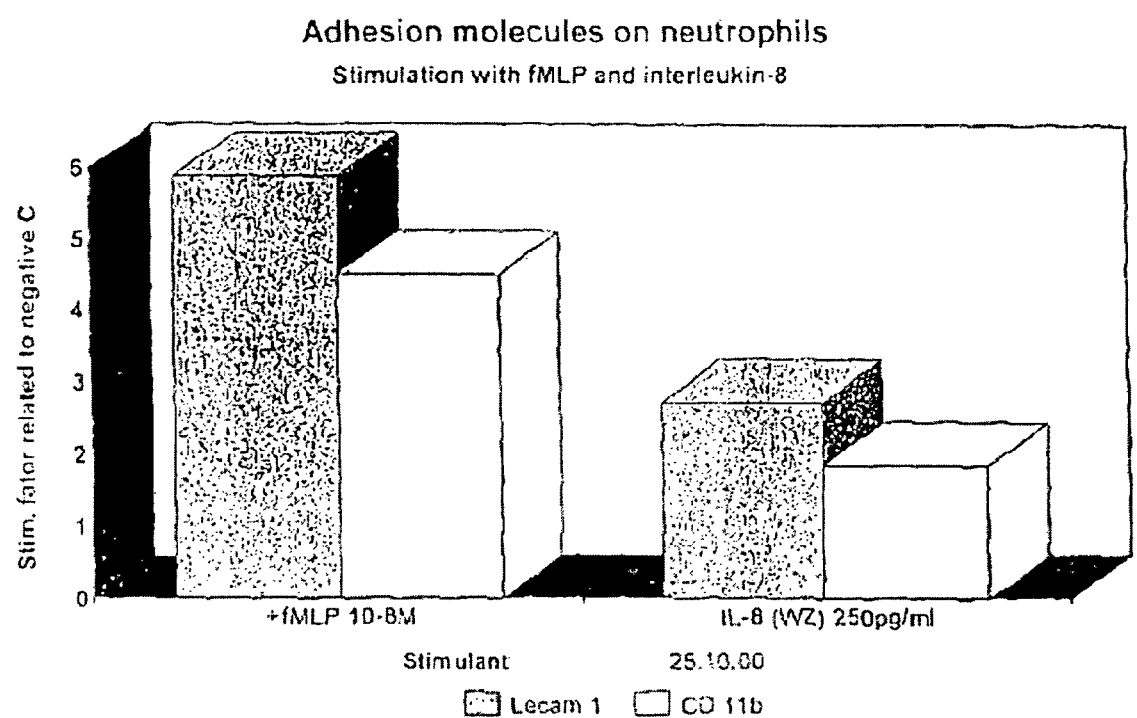

FIG. 6 shows adhesion molecules on neutrophils when stimulated with fMPL and interleukin-8.

The following examples clarify the invention further.

EXAMPLE 1

Granulocyte Function Test for Chemotaxis from Leukocyte-Rich Plasma 1.1 Enrichment 1 ml of Ficoll (Ficoll separation medium, from Seromed, order No. L6113 (endotoxin-low)) is initially introduced in an Eppendorf tube and 1 ml of fresh (preferably not older than 8 hours) heparinized whole blood (endotoxin-low heparin) is carefully overlaid at room temperature. The mixture is allowed to stand at room temperature until a marked phase separation can be observed. After a spontaneous sedimentation, normally lasting for about 40 minutes at room temperature, the leukocytes and platelets remain above the Ficoll phase while the erythrocytes have sedimented to the bottom. The sinking of the erythrocytes occurs quite suddenly after from approx. 30 to 40 minutes. If an older blood sample, for example a blood sample from the previous day, is used, the sedimentation process then lasts substantially longer.

Approx. 500 µl of the cell suspension forming the upper phase are removed and stored on ice, where appropriate. This phase is a leukocyte-rich plasma (LRP).

1.2 Stimulation and Chemotaxis

350 µl of PBS (phosphate-buffered salt solution without calcium and magnesium; e.g. from Biochrom, Berlin), as the negative control, and 350 µl of $5 \times 10^{-8}$ M fMLP (prepared from a $10^{-3}$ M stock solution, prediluted 1:20000 in PBS), for the assay, are initially introduced, per patient, in a cell culture plate possessing wells (for example a 24-well plate). In order to increase accuracy, at least two assays per patient are to be recommended. In addition, a healthy control volunteer should be assayed together with the patient so as to improve the test results.

As an alternative, interleukin 8 (IL-8) can, for example, be used as the stimulant, at a concentration of between 1 and 100 U/ml.

A membrane is inserted into each well of the well plate and in each case 100 µl of the cell suspension obtained under 1.1 is aliquoted onto this membrane. The membrane which is preferably used is a cell culture insert having a defined pore size. The cell suspension can be aliquoted in using a pipette, for example.

For stimulation, the plate is preferably incubated in a water bath at 37° C. for 20 minutes. The cells which have migrated through the membrane are then harvested. To do this, the inserts are tapped off and taken out and the cell suspensions are transferred into FACS tubes. The tubes can be placed on ice for storage.

1.3 Labeling

10 µl of the monoclonal antibody LECAM-1 FITC (e.g. Immunotech, order No. 1231) are added to the transferred cells and the mixture is vortexed. It is subsequently incubated at 4° C. for 15 minutes on ice.

As an alternative, it is possible to use 10 µl of CD11b-FITC.

1.4 Measurement

20 µl of LDS (laser dye LDS 751, from Exiton or Styryl 8, from Lambda Physik, Göttingen; for excluding the erythrocytes, 1 mg/ml, prediluted 1:50 in PBS) are added to the solution. In parallel, counting particles (Calibrite calibration particles, Becton Dickinson, order No. 349502) are vortexed for at least 20 seconds and 10 µl of counting particle solution are added to the mixture. The mixture is then incubated for approx. 10 minutes. Measurement then takes place on a flow-through cytometer (e.g. FACScan), with the stability of the test sample being at least 2 hours on ice in the dark. The measurement is stopped after in each case 1000 or 2000 latex particles have been recorded, such that approx. 5000-15 000 neutrophils have been counted. The measurement performed on the flow-through cytometer (e.g. FACScan) is to a large extent equivalent to the procedure when measuring immunofluorescence for the purpose of typing lymphocytes. The sheath fluid employed is FACS Flow (from Becton Dickinson, order No. 342003) or another carrier fluid having a low intrinsic fluorescence. The amplifier and compensation settings are effected by way of Autocomp software using unstained, FITC-stained and PE-stained microparticles (beads) or manually. The PMT voltages are changed. The unstained beads lie in the first decade, separate from the zero channel, and the FITC-stained and PE-stained beads in each case lie at approximately the center of the scale (channel 100). The calibration and quality control for fluorescence measurements (intensity per cell) are carried out using the Calibrites. The CellQuest program is used for data recording and evaluation. For the evaluation, a window is placed around the granulocyte population. The labels are set such that the evaluation region encloses the region within the half-maximal peak values. In addition, the mean value of the intensity of the forward light scatter (FSC) of the granulocytes is viewed in the side light scatter (SCC) against narrow-angle forward light scatter (FSC) plot.

A second region is placed around the cell particles, for the purpose of counting the cells, and acquisition is performed until 1000 and 2000 events, respectively, have been recorded in this region. The number of granulocytes in the PBS control and in the fMLP mixture can then be compared directly with each other.

The method according to the invention assesses the fluorescence intensity, i.e. a quantitative immunofluorescence is measured.

That which is assessed is the decrease in the fluorescence of the LECAM-1 in the fMLP or IL-8 mixture as compared with the PBS mixture in the case of a patient and in the case of a healthy control volunteer, and the increase in the FSC signal (cf. FIG. 3).

When CD11b is used, the density of expression of the antigen is increased. However, the relative change is much more clearly pronounced in the case of CD62.

EXAMPLE 2

Chemotaxis Test in Whole Blood

In order to determine the chemotactic activity of granulocytes in whole blood, the above-described protocol is amended as follows:

lithium heparin blood is cooled on ice in order to prevent the granulocytes being preactivated. 100 µl of whole blood are pipetted, per assay, into a FACS tube. 20 µl of an fMLP solution (predilution 1:5000) or 20 µl of RPMI medium or HESS buffer (HBSS (Hank's buffered sodium chloride solution; e.g. from Life Technologies, Catalog No. 24020)), as the negative control, are added to the whole blood sample. The samples are mixed briefly on a vortex mixer. The samples are then incubated in a water bath at 37° C. for 15 minutes. The samples are then placed on ice to stop the reaction. In each case, 10 µl of LECAM-1-FITC are then added. After they have been thoroughly mixed (vortexing), the samples are incubated in an ice water bath for 15 minutes while excluding light. After that, 3 ml of $NH_4Cl$ lysis solution ($NH_4Cl$ lysis solution (10× stock solution in 1 l of double-distilled water, 89.9 of $NH_4Cl$, 10.0 g of $KHCO_3$, 370.0 mg of EDTA) are added in each case. The samples are mixed on the vortex mixer and incubated at room temperature for 5 minutes. After that, the samples are washed twice, by centrifugation (5 minutes, 250×g), with RPMI medium or HBSS buffer. After that, 20 µl of LDS are added in each case and the samples are incubated on ice for 5 minutes. Flow-through-cytometric measurement is then used to determine the decrease in LECAM-1 fluorescence and the increase in the FSC signal.

EXAMPLE 3

Use of Coated Membranes for Measuring Transmigration

The chemotactic activity was carried out as described in example 1, with variously coated membranes being inserted into the cell culture well plate. The coatings were applied to the membranes by immersing the membranes, for 30 minutes, in dilute solutions of the respective coating materials in PBS (phosphate-buffered salt solution) and then drying the membranes in a drying oven. FIG. 4A shows results which were obtained for various membrane coatings applied to polycarbonate membranes (Nunc tissue culture inserts, polycarbonate membranes, order No. 137370, diameter 10 mm, pore size 3.0 µm). FIG. 4B shows the results of using a commercially obtainable collagen-coated cell culture insert (Collagen (BD); Falcon cell culture inserts, PET (polyethylene terephthalate) membrane, order No. 354545, diameter 6.4 mm, pore size 3.0 µm, coated with mouse collagen IV), and also Falcon polyethylene terephthalate membranes (order No. 353096) which were coated with Tween20 or collagen.

As can be seen from FIG. 4A and FIG. 4B, it is possible to achieve a marked improvement in the results, in particular a marked improvement in the differences in the number of cells migrating through the membranes in the presence of stimulant (sMLP) and in the absence of stimulant (only PBS) when coated membranes, in particular collagen-coated membranes, are used.

The invention claimed is:

1. A method for diagnosing an immunological defect or a disturbance in leukocyte function in a subject, comprising:
   (i) providing a leukocyte containing sample from said subject;
   (ii) pre-incubating said sample with a chemotaxis stimulant;
   (iii) conducting said leukocytes through a porous membrane wherein said porous membrane is coated with collagen, fibrinogen or gelatin;
   (iv) determining in a flow-through cytometer;
      (a) any change in shape or size of the leukocytes, and
      (b) the number of leukocytes which have migrated through said porous membrane; and
   (v) comparing the results from (iv) to a control, wherein differences therebetween indicate an immunological defect or a disturbance in leukocyte function in said subject.

2. The method of claim 1, wherein said leukocyte is a granulocyte.

3. The method of claim 2, wherein said granulocyte is a neutrophilic granulocyte.

4. The method of claim 1, wherein said chemotaxis stimulant is fMLP or interleukin-8.

5. The method of claim 1, wherein said leukocyte containing sample is anticoagulated whole blood or leukocyte-rich plasma.

6. The method of claim 1, comprising determining the number of leukocytes which have migrated through said porous membrane by adding latex beads to the flow-through cytometer.

7. The method of claim 1, wherein said immunological defect or disturbance in leukocyte function results in recurrent skin abscesses.

8. The method of claim 1, wherein said immunological defect or disturbance in leukocyte function results in a disturbance in wound healing.

9. The method of claim 1, further comprising determining expression of CD62L on the surface of said leukocytes.

10. The method of claim 9, comprising determining a molecule which binds specifically to CD62L.

11. The method of claim 10, wherein said molecule is an antibody.

12. The method of claim 11, wherein said antibody is labeled with a fluorescent label.

* * * * *